(12) United States Patent
Vieira

(10) Patent No.: US 6,487,367 B2
(45) Date of Patent: *Nov. 26, 2002

(54) EVAPORATION DEVICE FOR VOLATILE SUBSTANCES

(75) Inventor: Pedro Queiroz Vieira, Parede (PT)

(73) Assignee: C.T.R. Consultoria Técnica e Representacöes Lta., Almargem do Bispo (PT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/919,125

(22) Filed: Jul. 31, 2001

(65) Prior Publication Data

US 2002/0146242 A1 Oct. 10, 2002

(30) Foreign Application Priority Data

Apr. 5, 2001 (EP) .............................. 01107796

(51) Int. Cl.[7] .............................. F24F 6/08; F24F 6/00
(52) U.S. Cl. ........................................ 392/395; 392/392
(58) Field of Search .................................. 392/386, 390, 392/392, 394, 395, 402, 403; 261/94, 99, DIG. 65; 219/543, 544, 546, 547; 338/286, 307, 308

(56) References Cited

U.S. PATENT DOCUMENTS

| | | | | |
|---|---|---|---|---|
| 1,154,113 A | * | 9/1915 | Hadaway, Jr. .............. | 392/395 |
| 2,715,056 A | * | 8/1955 | Wilson .......................... | 422/4 |
| 3,440,589 A | * | 4/1969 | Minks ........................ | 174/52.2 |
| 3,633,881 A | * | 1/1972 | Yurdin ........................ | 261/24 |
| 3,672,568 A | * | 6/1972 | Foote ......................... | 392/395 |
| 5,038,394 A | * | 8/1991 | Hasegawa et al. .......... | 392/395 |
| 5,222,186 A | * | 6/1993 | Schimanski et al. ........ | 392/395 |
| 5,264,681 A | * | 11/1993 | Nozaki et al. .............. | 219/270 |

FOREIGN PATENT DOCUMENTS

| | | |
|---|---|---|
| EP | 0 943 344 A1 | 9/1999 |
| EP | 0 962 132 A1 | 12/1999 |
| WO | WO 98/19526 | 5/1998 |
| WO | WO 98 58692 | 12/1998 |

* cited by examiner

Primary Examiner—Sang Paik
(74) Attorney, Agent, or Firm—McNair Law Firm, P.A.; Cort Flint

(57) ABSTRACT

A device for the evaporation of volatile substances, in particular of insecticides and/or aromatics, is disclosed having a housing containing a heating element, with a container for the volatile substance disposed in the housing, a wick which can be heated by the heating element, and a heating block having a wick end protruding from the container along a wick axis. The improved device includes at least one additional wick opening formed within the heating block; at least one additional container for containing an additional volatile substance for evaporation, and the additional wick opening being operatively associated with the additional container. At least one additional wick is carried in the additional container, having a wick end extending through the additional wick opening for evaporation of the additional volatile substance in the additional container.

29 Claims, 5 Drawing Sheets

B-B

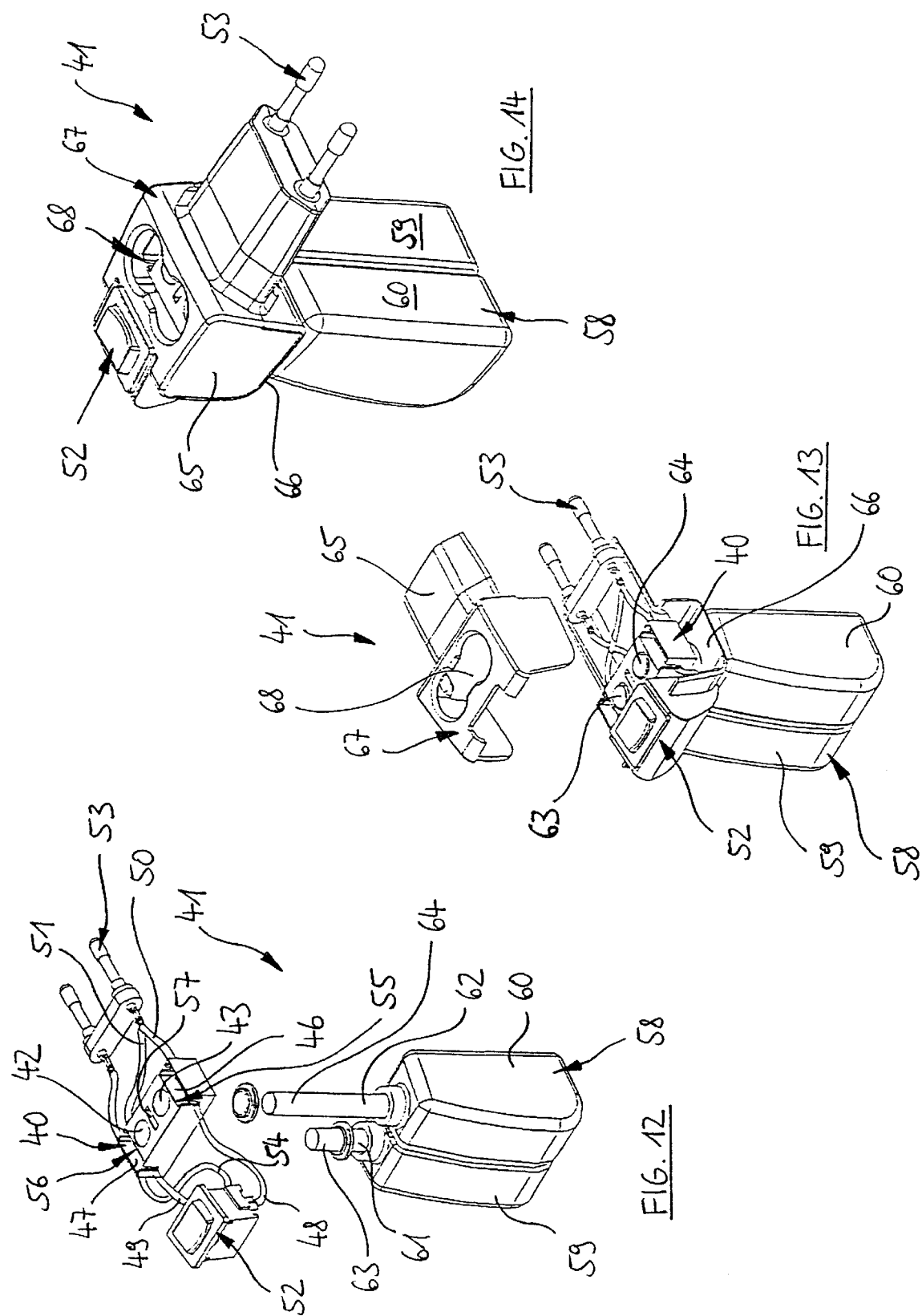

EVAPORATION DEVICE FOR VOLATILE SUBSTANCES

BACKGROUND OF THE INVENTION

The present invention relates to a device to evaporate volatile substances, in particular insecticides and/or aromatics.

Devices of this type for evaporation of volatile substances are generally known. For example, evaporation devices are known where a small plate is introduced into an evaporation device, impregnated with an active ingredient, and heated in order to evaporate the active ingredient. Another known method utilizes a container for retaining a volatile substance within the housing of an evaporation device. The container utilizes a wick that, via capillary action, conveys the substance to be evaporated out of the container. The container is located next to a heating element such as a ceramic block, and the wick end protrudes from the container so that the substance is evaporated via radiant heat emitted by the heating element. The evaporate then escapes from the housing into the surrounding environment via aeration slits in the housing.

European patent 0 943 344 A1 discloses such as device for the evaporation of volatile substances, in particular of insecticides and/or aromatics. The disclosed device utilizes a housing with a heating apparatus that incorporates a ceramic heating block as its heating element. The disclosed device further utilizes a container for retaining a substance to be evaporated. The container can be connected to the housing, and a wick can be inserted into the container. The operative function of the disclosed device requires the wick end to protrude from the container and into a wick recess within the heating block to effect the evaporation of the substance within the container.

The disclosed device further consists of a plug element with a connecting plug. The plug element threads into the same housing the container is also inserted. Pin openings on the housing and locking pins join to mesh with the threads of the plug element. This allows the distance between the resistance-heating element connected to the plug element and the wick end protruding from the container to be altered by twisting the plug element. In one disclosed embodiment, the plug is mounted eccentrically in the housing element, so that it too can be used to change the relative distance between the wick end and the resistance-heating element, depending on the desired evaporation rate. Evaporation devices of this type (into which a container is inserted) suffer many problems and disadvantages. One such disadvantage is that only a single substance can be evaporated at a time. For instance, aromatherapy often requires two, or possibly more, aromatics be evaporated simultaneously. Currently, depending on the number of the aromatics to be mixed and evaporated, a corresponding number of such evaporation devices must be used. The utilization of several evaporation devices is also required for the evaporation of two different insecticides designed for specific types of insects.

A further disadvantage of previous evaporation devices, is the relatively expensive and complicated manufacturing costs surrounding the manufacture of evaporation devices capable of adjusting the evaporation rate. Previous evaporation devices are rather costly to manufacture.

The disadvantages and limitations of previous evaporation devices are disclosed in WO 98/58692, WO 98/19526 and EP 0 962 132 A1, which disclose the same concept as EP 0 943 344 A1; allowing adjustability of the evaporation rate by changing the position of the wick relative to the heating block.

A common feature of all these known evaporation devices is their impractical large size. Their large size is particularly impractical and unaesthetic for residential use. The large construction of previous evaporation devices require a great number of components to effect adjustment of the evaporation rate. The numerous components are easily lost and render the devices difficult to repair.

Accordingly, an object of the present invention is to provide an evaporation device for evaporating volatile substances, in particular insecticides and/or aromatics, which allows for more than one volatile substance to be evaporated simultaneously, allows adjustability of the evaporation rate, has a reduced size and improved aesthetic quality for residential use, and is relatively easy and inexpensive to manufacture.

SUMMARY OF THE INVENTION

The above object is accomplished according to the present invention by providing an improved evaporation device, in particular for insecticides and/or aromatics, of a type having a housing containing a heating element, with a container for the volatile substance to be evaporated disposed in the housing, and a wick which can be heated by a heating block. The wick has a wick end protruding from the container along a wick axis. At least one additional container for retaining an additional volatile substance is provided. A wick recess is assigned within the heating block to each container. There is a wick inserted in each container. The wick ends of the wicks extend into the wick recesses for evaporation of the volatile substances retained within the containers.

An advantage of the present evaporation device at least one additional wick recess is provided. Each additional wick recess is assigned to an additional container with a wick inserted into it. A wick end of the additional wick extends into the additional wick recess for the evaporation of the volatile substance contained in this additional container. The present innovation advantageously achieves the evaporation of two or more volatile simultaneously within a single device. Depending upon the application, the plural volatile substances could be two or more aromatics for aromatherapy, or two or more different aromatics for the improvement of room air. In the same manner, two or more insecticides could simultaneously evaporate within the present innovation. The present innovation ensures the heating block is heated by the heating element so an evaporation temperature radiates to the wick recess, ensuring evaporation of all substances, regardless of their evaporation temperature.

The present innovation does not require multiple volatile substances for evaporation to operate, and if the evaporation of only one single substance is desired, it suffices to merely insert one container with a single volatile substance into the housing. Furthermore, the present innovation can evaporate identical volatile substances in two or more different containers, so that a quicker evaporation of a greater quantity of volatile substances can be achieved using a single device. This use may be required, for instance, in large spaces. The present innovation contemplates more than two wick openings with corresponding container wicks extending into the heating block. In a preferred embodiment, the housing has two containers, each with a wick. For this embodiment two wick openings are formed in the heating block. A wick end of the wick associated with each container extends into each opening. In principle, each container can be two vessels, each with one single wick. An alternative embodiment, however, utilizes a single vessel having two chambers separated from each other as the container. This alternative embodiment allows different substances to be evaporated simultaneously.

The present innovation contemplates a small-sized and well-suited heating element with good heating performance. In a preferred embodiment, the heating element is an electric resistance element contained within the heating block. In a preferred embodiment the wick end is assigned to the heating block via a wick recess in form of a passage opening or as a recess on the edge of the heating block. In a preferred embodiment the heating element is placed approximately in the middle between two wick openings. The heating block preferably has a rectangular or oval form, and is located approximately in the center of the heating block so that the wick recesses are located on either side of the heating element. This preferred embodiment ensures proper heat conductivity in the direction of the two wick openings to achieve optimal evaporation of the two or more volatile substances. The heating block temperature should then be at least as high as the evaporation temperature of the volatile substance that has the highest evaporation temperature. It is sufficient, however, if the heating block is designed so that the desired respective evaporation temperature prevails in the areas of the wick openings, as may also be the case with different temperatures in different heating block areas.

Another advantage of the present innovation is uniform and effective evaporation with a good mixing of two different volatile substances obtained when the wick openings are identical and equidistant from the heating element in a preferably symmetrical placement about the heating element.

In a preferred embodiment of the present innovation, at least two heating elements are provided in the heating block. Each heating element has at least one wick recess which constitutes one heating unit. The heating elements are connected to a switching and/or control device through which the heating element can be deactivated or actuated as needed. The heating elements can be deactivated or actuated separately. This preferred embodiment affords greater flexibility and better functional integration because a plurality of individual heating units, each consisting of heating element and wick recess, can be integrated into one single apparatus.

Another advantage of the present innovation is the heating element can be associated with a wick recess. It is also possible, however, for one wick recess to be assigned more than one heating element, each having different heating capacities, so that different evaporation rates may be assigned depending on which assigned heating element is actuated. If necessary, all the heating elements can be actuated together, or only single ones actuated. It is also possible to assign several wick openings to one heating element, so that several wick recess areas can be heated to evaporation temperature through a single heating element, if necessary.

Another advantage of the present innovation is the individual heating elements are able to produce different temperatures, and thereby different evaporation rates. Thus, heating elements with different heating capacities can be used. This allows a simple and economical alternative to the evaporation devices known from the state of the art, where the degree of evaporation can be adjusted only in a complicated and expensive manner with mechanical devices by adjusting relative distances. Alternatively, the utilization of identical heating elements, producing an identical rate of evaporation may be used when different substances with approximately the same evaporation temperature are to be evaporated.

Another advantage of the present innovation is the electrical resistance elements preferably approximate a rod shape and are incorporated within the heating block approximately parallel to each other. Utilizing rod-shaped electrical resistance units oriented approximately parallel about the heating block ensures proper heating of the heating block, especially where, in a preferred embodiment, a ceramic heating block is used. Furthermore, the rod-shaped resistance elements take up very little space, adding to the compact design of the present innovation.

Another advantage of the present innovation is the various possibilities for the placement of the wick openings, as well as of the corresponding heating elements on the heating block. To actuate and deactivate the individual heating units without having one heating unit cross-heating to the evaporation temperature of the other heating unit, in particular in the area of the passage opening. The present innovation places the two wick openings at a distance from each other, and in the center between two heating elements, preferably located at the edge of the heating block to ensure cross-heating does not occur.

In an alternative embodiment thermal uncoupling the different heating elements may be enhanced by including at least one separating element between the two wick openings for the at least partial thermal uncoupling of the two heating units. The preferred separating element is an air gap going through the heating block at least in the area between the two wick openings. This process of thermal uncoupling is also possible in evaporation devices in which more than two heating units are utilized.

Another advantage of the present innovation is using at least two heating elements, where each of the heating elements can provide a different heating capacity for different substances to be evaporated. Thus where electric resistance elements serve as the heating elements, they can have different resistance values. The desired evaporation rate can be easily set in this manner. Alternatively, two identical resistance elements can also be provided for the evaporation of substances with approximately the same evaporation temperature.

Another advantage of the present innovation is the various possibilities for the placement of the switching and/or control device, depending upon the desired application. For a compact, small-size device, the switching and/or control device can be integrated directly into the housing, and can be in form of a manual switch. Alternatively the switching and/or control device may be a programmable microprocessor connected to the device, or to the housing.

The present innovation contemplates connecting the heating element to a power source via electrical lines to a connection plug located on the housing.

Another advantage of the present innovation is the resistance element can consist of any known resistance element, e.g. PTC resistances. In a preferred embodiment, an electrical resistance element is provided by a rod-shaped resistance body covered at some areas with a resistance layer that is notched and/or machined off in spots, to set a given resistance value. The resistance value may be adapted to the evaporation temperature for the composition of the volatile substance in order to provide a heating device with small dimensions. This results in an overall miniaturized device for the evaporation of volatile substances. A resistance element of this type for heating units can advantageously be relatively small in size so that the heating block and the heating unit, and the entire housing, may be relatively small in size. Thereby miniaturized evaporation devices can be created while using at the same time one or two or more suitably adapted low-volume containers in the housing. Thanks to the reduced expenditure for material and components, such a miniaturized evaporation device can also be produced relatively simply and thereby inexpensively, e.g. as a disposable item.

Another advantage of the present innovation is the evaporation temperature can be adjusted optimally to the composition of the volatile substance at any time with a resistance element of this type by cutting or grinding the resistance layer to provide the setting of a given resistance value at different locations. This reduces the flammability danger of the overall device, and in addition, reduces a possible negative effect on the degree of evaporation.

The present innovation contemplates various mechanisms for notching or grinding the resistance layer to set a given resistance value. In a preferred embodiment, the resistance layer is cut into and around the rod-shaped resistance body in a helicoidal form, preferably by helicoidal laser cutting. With such a helicoidal cut the resistance value can be adjusted very precisely and easily for optimal evaporation performance. The resistance layer can also be constructed of different materials, e.g. in form of a special metal layer. In a preferred embodiment, however, the resistance layer is a metal oxide layer, preferably a nickel-chrome alloy layer, which is burned on thermo-chemically by vacuum metalizing or cathodic sputtering in form of a-thin layer. After the resistance layer has been applied, it is preferably subjected to a thermal process in order to stabilize the resistance layer. The resistance body can be made or ceramic in this case, preferably with a high content in AL203 (aluminum oxide), to ensure proper heat conductivity of the resistance body is achieved. The AL203 content depends upon the actual installation conditions e.g. the housing material, the wick material, etc. being used.

The present innovation also contemplates metal caps placed on the ends of the coated, rod-shaped resistance body, and preferably pressed on. An electrical line is connected, preferably welded to each of these caps that is in turn connected to the connection plug. Copper wire with good electrical conductivity is preferably used for the electric lines.

Another advantage of the present invention is the various possibilities for the installation of the rod-shaped resistance element on the heating block. In a preferred embodiment, the rod-shaped resistance element is inserted into a recess within the heating block. The resistance element is encapsulated therein using a highly heat-conductive material, fixing the resistance element in the heating block. The fixing material is preferably a flame-resistant insulation cement. In a preferred embodiment, slits are preferably formed on either side of the resistance element at the opposite ends of the recess. The electrical lines pass out of the heating block and go through these slits to the connection plug. This embodiment allows easy insertion of the resistance element during assembly. In a preferred embodiment the present innovation incorporates a clamping lock, so the resistance element cannot slip during the encapsulating process. Furthermore, the electric lines can easily be curved in the direction of the connection plug. The electric lines can be insulated in a conventional manner.

Another advantage of the present innovation is simple and rapid assembly of the heating device within the housing. In a preferred embodiment, the housing is made up of at least two parts, an upper shell and a lower shell connected by means of locking and/or clip elements. The lower shell preferably contains connecting means to connect the container to the housing locking elements. At least one of the two shells has aeration slits for the escape of the evaporated substance into the environment. In a preferred embodiment the aeration slits are made in the area above the wick end in the upper shell.

BRIEF DESCRIPTION OF THE DRAWINGS

The construction designed to carry out the present invention will hereinafter be described, together with the features thereof.

The invention will be more readily understood from a reading of the following specification and by reference to the accompanying drawings forming a part thereof, wherein an example of the present invention is shown and wherein:

FIGS. 12, 13 and 14 show the step-by-step assemblage of an evaporation device with a heating device according to FIGS. 9, 10 and 11.

DESCRIPTION OF A PREFERRED EMBODIMENT

Figure 1:
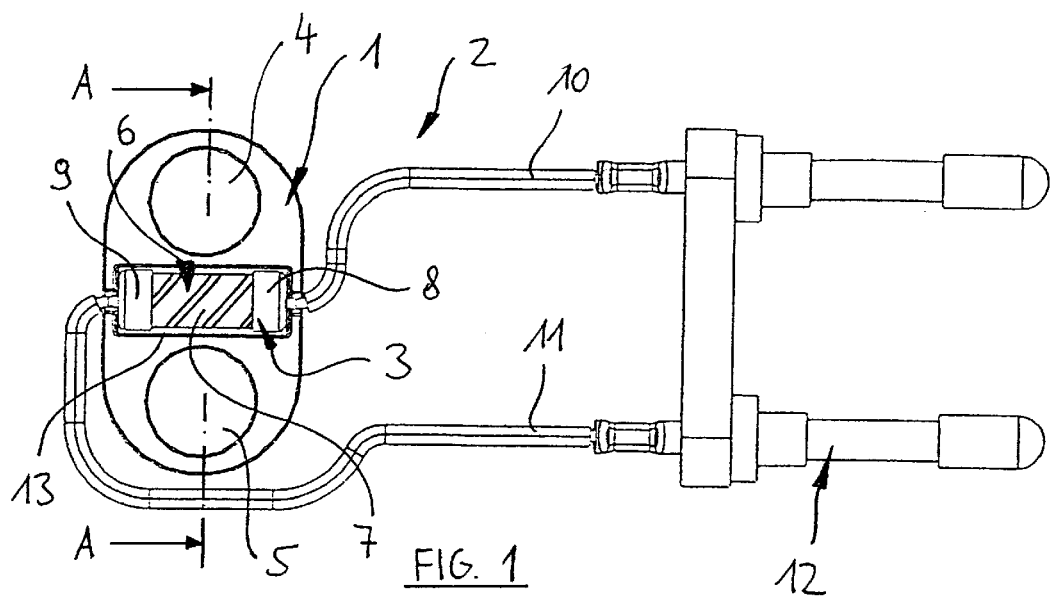
FIG. 1 is a schematic enlarged top view of a heating device with a heating block with two wick openings and one central heating element ATI=according to the invention.

Referring to the drawings, the invention will now be described in more detail. In the drawings, like numbers represent like elements throughout the several views. A preferred embodiment of the present innovation is depicted in FIG. 1 through FIG. 14.

Figure 2:
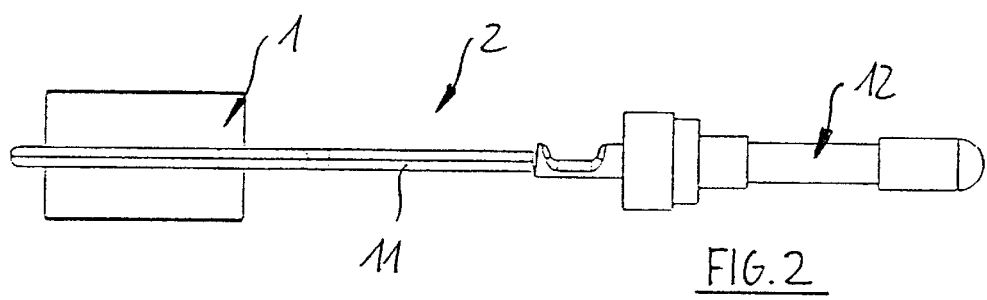
FIG. 2 is a schematic side elevation of the representation in FIG. 1.
Figure 3:
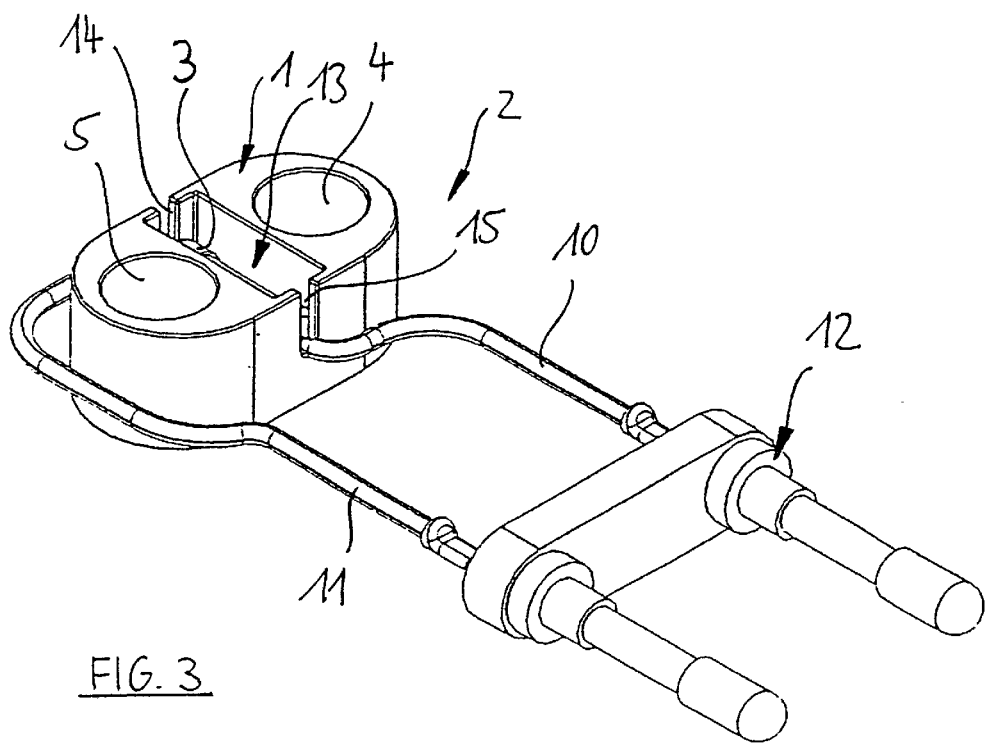
FIG. 3 is a schematic, perspective view of the heating device of FIGS. 1 and 2.
Figure 8:
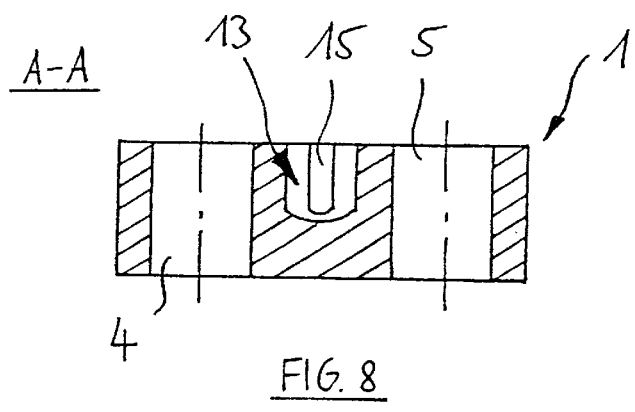
FIG. 8 is a schematic cross-section through a heating block along line A—A of FIG. 1.

FIGS. 1, 2 and 3 illustrate different views of an evaporation device 2 for the evaporation of volatile substances, in particular of insecticides and/or aromatics ATI which includes a heating device 1. FIG. 3 shows the heating device having a heating block 1, which is preferably made of ceramic, having a generally oval form. An electric resistance element 3, serving as the heating element, is located approximately in the central area of the heating block 1 as seen from above. Two wick openings 4, 5 form passage openings in the heating block 1. The wick openings are identical and equidistant from the resistance element 3. This provides a symmetric placement of the wick openings 4, 5 about the resistance element 3. FIG. 8 is a section through the heating block 1 along line A—A.

Figure 7:
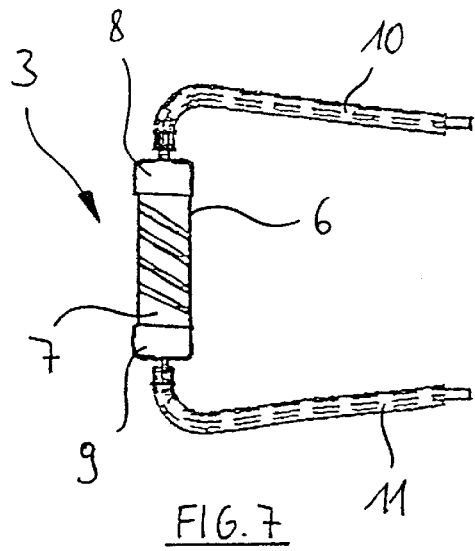
FIG. 7 is a schematic top view of a heating element in the form of an electric resistance element ATI.

FIG. 7 illustrates resistance element 3 schematically without heating block 1. A rod-shaped resistance body 6 is preferably made of ceramic with a certain content of A1203, and is coated with a resistance layer 7 of metal oxide, e.g. a nickel-chrome alloy layer. To set a given resistance value, this resistance layer 7 is cut in a helical form into resistance layer 7, preferably by means of laser spiral cutting, so that a helicoidal cut is formed around cylindrical resistance body 6. A metal cap 8, 9 is preferably pressed on either end of the coated, rod-shaped body 6 for an electrical connection to resistance layer 7. An electric line 10, 11, preferably insulated copper wire, is welded to each cap 8, 9.

FIGS. 1, 2 and 3 illustrate resistance element 3 connected to a connection plug 12 through electrical lines 10, 11. Resistance element 3 can be inserted into a central recess 13 in heating block 1, and is preferably encapsulated with a highly heat-conductive material, e.g. a flame-resistant insulation cement. FIGS. 1, 3 and 8 illustrate slits 14, 15 at the opposite recess walls, on either side of the resistance element 3. Electrical lines 10, 11 pass through slits 14, 15 and exit the heating block 1 for connection to connection plug 12.

Figure 4:
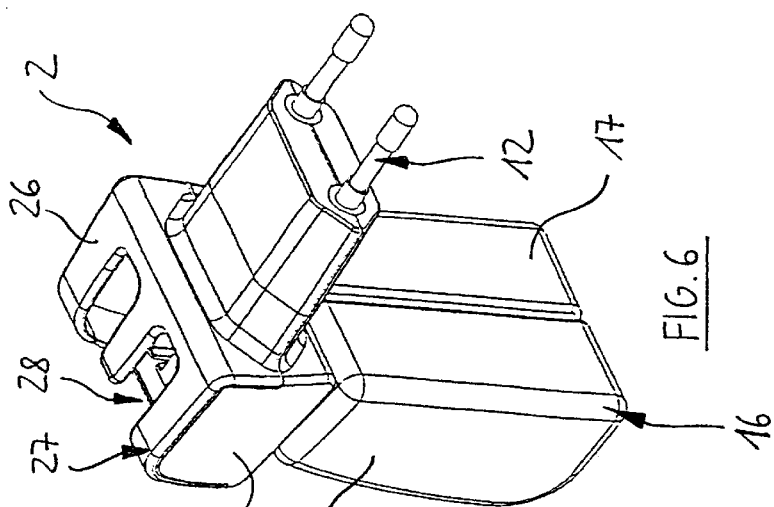
FIG. 4 is a schematic perspective view of a container with two chambers, and a wick assigned to each chamber ATI, as well as of a heating device according to FIGS. 1, 2 and 3.
Figure 5:
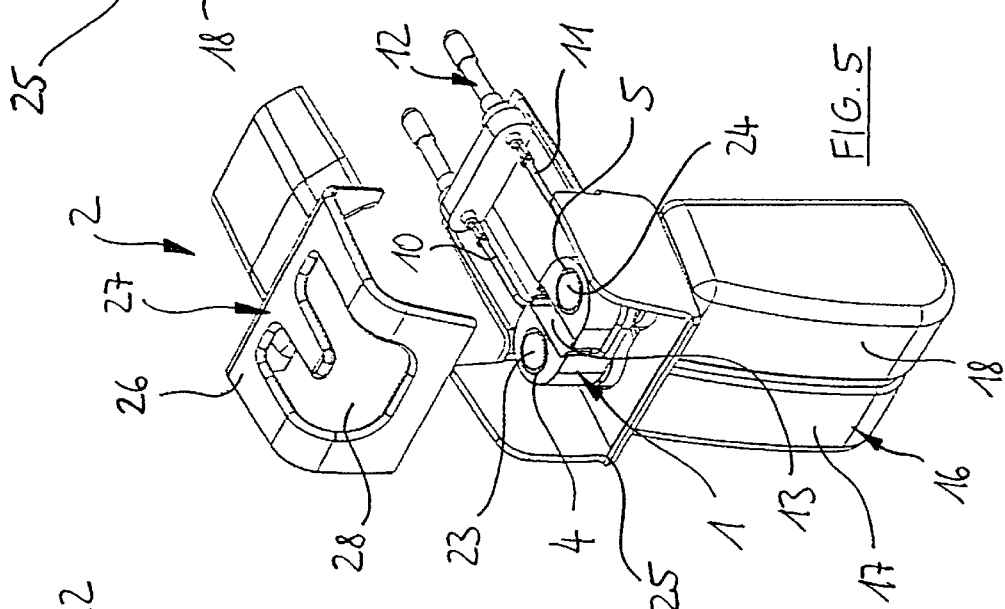
FIG. 5 is a schematic perspective view according to FIG. 4 illustrating the heating device mounted on the lower shell of a housing.
Figure 6:
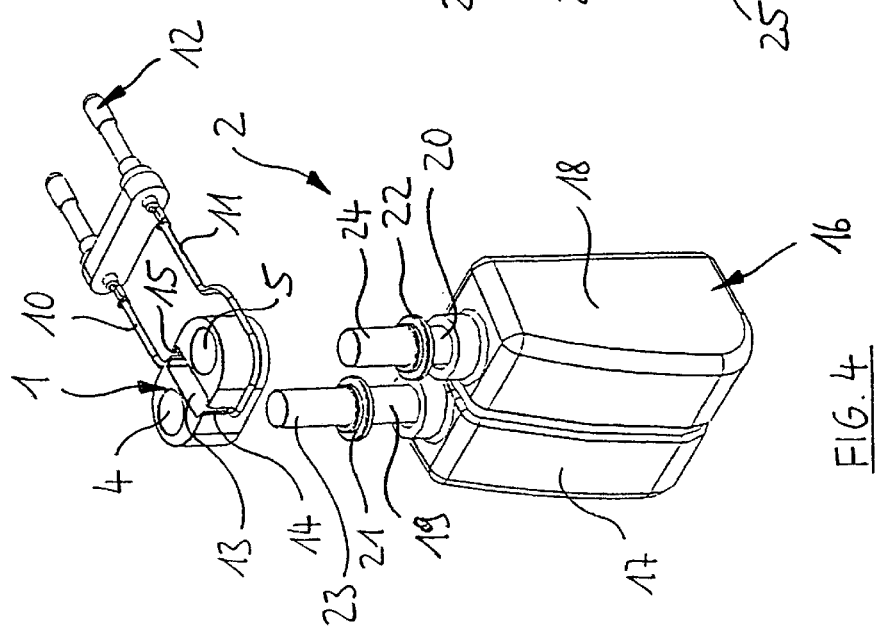
FIG. 6 is a schematic perspective view corresponding to FIGS. 4 and 5 illustrating a completely assembled device ATI.

FIGS. 4, 5 and 6 illustrate an alternate embodiment of an evaporation device 2 which comprises a container 16 having two chambers 17, 18 separated from each other. Different substances which may be evaporated are contained in these chambers. As can best be seen in FIG. 4, a wick 19, 20 can be inserted into each chamber 17, 18, and held by a wick holder 21, 22 on the chambers 17, 18. A wick end 23, 24 protrudes from chambers 17, 18.

FIGS. 5 and 6 illustrates evaporation device 2 with housing 27 having a lower shell 25 and an upper shell 26 which contain the heating device and heating block 1. FIG. 5 illustrates the assembly wherein container 16 is connected to the lower housing shell 25 and heating block 1 so that wick ends 23 and 24 extend into wick recesses 4 and 5 of the heating block 1. Upper housing shell 26 is then clipped together with the lower housing shell 25 so that a completely assembled evaporation device 2, as shown in FIG. 6, is provided. As can best be seen, FIGS. 5 and 6, aeration slit 28 in the upper housing shell 26 allow the evaporated substances to escape into the environment.

During the operation of evaporation device 2, heating block 1 is heated to an evaporation temperature in the area of the wick openings 4, 5. The substances conveyed by means of the wicks 19, 20 extending from chambers 17, 18 are properly evaporated. In an aromatherapy, for example, two different aromatics can be placed in chambers 17, 18 and both can then be evaporated together by means of evaporation device 2 to produce a mixture of aromatics. The same utilization is also possible with insecticides where insecticides adapted to different insects can be contained in two chambers 17, 18, for example, both of which can also be evaporated at the same time. As an alternative, it is however also possible to provide one container with wicks assigned to wick recesses 4, 5. In this case, operation of evaporation device 2 is also possible in the conventional manner, with one container.

Figure 9:
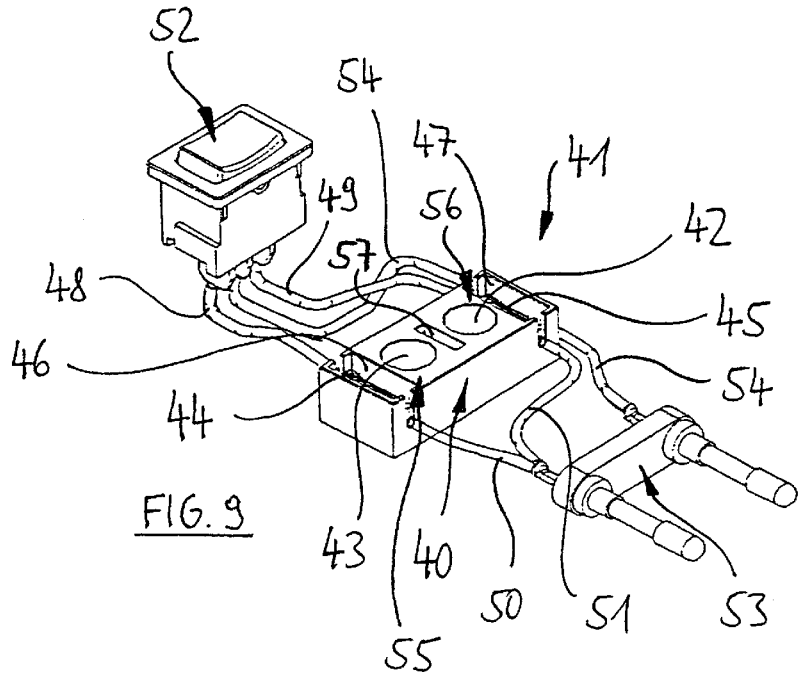
FIG. 9 is a schematic perspective view of an alternative embodiment of a heating device and heating block having two passage openings and two heating elements ATI.

FIG. 9 illustrates an alternate embodiment of a heating block 40 of an evaporation device 41. Heating block 40 has two wick openings 42, 43 at a distance from each other. As can best be seen in the top view of FIG. 10, heating block 40 is disposed in a central area between two resistance elements 44, 45 provided at the edges of the heating block. FIG. 11 illustrates a cross-section through the heating block 40 taken along line B—B of FIG. 10. The resistance elements 44, 45 are designed as resistance element 3. Preferably resistance elements 44, 45 have different resistance values.

Resistance elements 44, 45 are received in openings 46, 47 of the heating block 40 and are cemented in place therein. Electric connection lines 48, 49 as well as 50, 51 are assigned to each resistance element 44, 45. Electric lines 10, 11 pass through slits 14, 15 near the lateral recess walls so that connection line 48 of resistance element 44, as well as connection line 49 of resistance element 45, go to a manual switch 52. Alternately, connection line 50 of resistance element 44 and connection line 51 of resistance element 45 go to a connection plug 53. In addition, an electric line 54 goes from manual switch 52 to connection plug 53.

Figure 10:
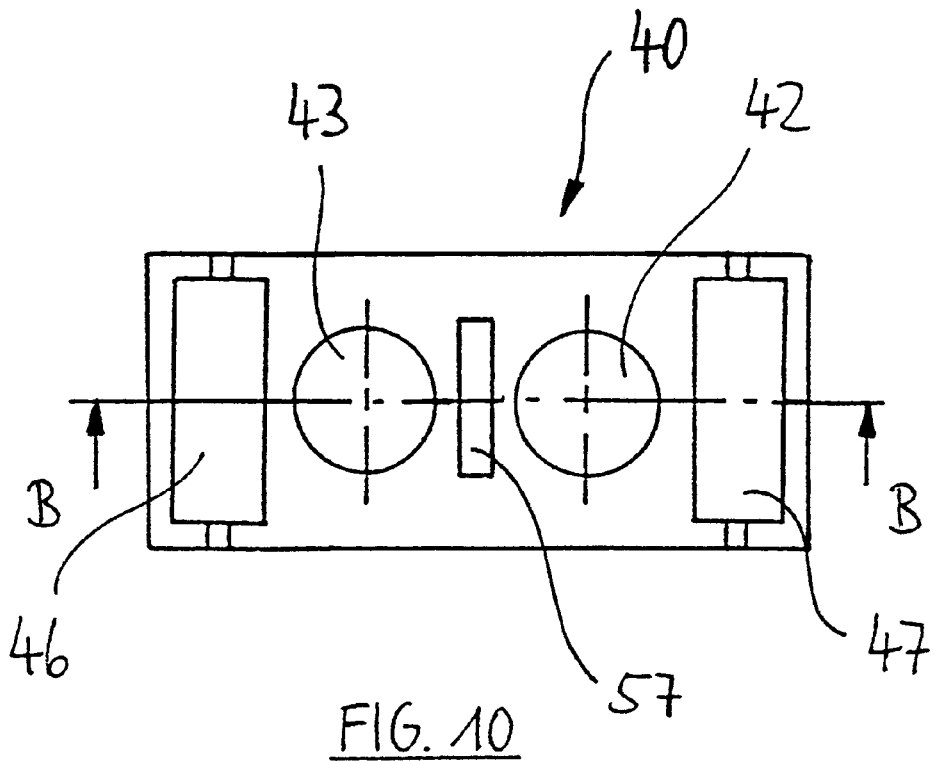
FIG. 10 is a schematic top view of the heating block of FIG. 9.
Figure 11:
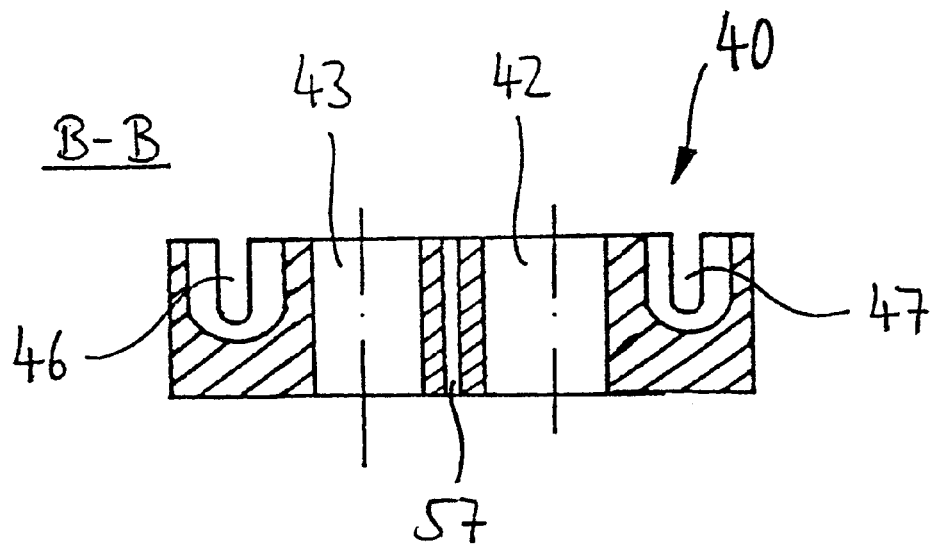
FIG. 11 is a schematic cross-section along line B—B of FIG. 10.

As can best be seen in FIGS. 9, 10 and 11, an air gap 57 is formed through heating block 40 between wick openings 42, 43 for the, at least partial, thermal uncoupling of heating units 55 or 56. Heating units 55, 56 include wick recess 42 and resistance element 44, as well as wick recess 43 and resistance element 45, respectively.

FIGS. 12, 13 and 14 illustrate an evaporation device 41 equipped with a container 58 having two chambers 59, 60. Chambers 59, 60 are assigned wicks 61, 62. In the assembled state, wick ends 63, 64 extend from chambers 59, 60. Preferably different volatile substances having different evaporation temperatures are contained in chambers 59, 60.

FIG. 13 illustrates evaporation device 2 in an assembled state with heating block 40 located in housing 67. Housing 67 consists of an upper housing shell 65 and a lower housing shell 66. A recess can be provided in housing 67 for the integration of manual switch 52. In addition, upper shell 65 is provided with an aeration slit 68.

Heating units 55, 56 can be actuated separately via manual switch 52, so that either the volatile substance in chamber 59 or in chamber 60 can be evaporated. The resistance value of elements 44 and 45 can be adapted to the substances in chambers 59 and 60 to be evaporated. The manual switch can further be provided with an additional switching position by which both heating units 55 and 56 are actuated so that, especially in an aromatherapy, a mixture of aromatics can be produced by evaporation from both chambers 59 and 60. In another switching position of manual switch 52 however, heating units 55 and 56 are deactivated.

While a preferred embodiment of the invention has been described using specific terms, such description is for illustrative purposes only, and it is to be understood that changes and variations may be made without departing from the spirit or scope of the following claims.

What is claimed is:

1. A device for the evaporation of volatile substances, in particular of insecticides and/or aromatics, of a type having a housing containing a heating element, with a container for the volatile substance disposed in the housing, a wick which is heated by the heating element, and a heating block having a wick end protruding from the container along a wick axis, and wherein the device comprises:

at least one additional wick opening formed within said heating block;

at least one additional container for containing an additional volatile substance for evaporation, and said additional wick opening being operatively associated with said additional container; and at least one additional wick carried in said additional container, having a wick end for extending through said additional wick opening for evaporation of said additional volatile substance in said additional container.

2. The device of claim 1 wherein said volatile substance comprises an insecticide.

3. The device of claim 1 wherein said volatile substance comprises an aromatic.

4. The device of claim 1 including an attachment element for attaching said additional container within said housing.

5. The device of claim 1 wherein said additional container includes a separate independent container.

6. The device of claim 1 wherein said additional container includes one of separate chambers made integral with a single container.

7. The device of claim 1 wherein said heating element comprises an electrical resistance element carried by said heating block.

8. The device of claim 1 wherein said additional wick forms a wick passage within said heating block.

9. The device of claim 8 wherein each said wick passage includes a bore extending through said heating block formed in and completely bounded by said heating block.

10. The device of claim 8 wherein each said wick passage is equidistant from said heating element so that wick passage placement is symmetrical about the heating element in said heating block.

11. The device of claim 1 wherein said heating block is one of rectangular and oval in shape.

12. The device of claim 1 wherein said heating element is located in the center of said heating block so that each said additional wick is located on equidistant sides of said heating element.

13. The device of claim 1 wherein said heating element includes an electrical resistance rod, wherein said resistance rod is substantially coated with a resistance layer which is patterned for providing a desired resistance value, whereby said resistance value corresponds to the evaporation temperature of said volatile substance to be evaporated.

14. The device of claim 13 including a plurality of heating elements disposed within said housing;

a heating block associated with said heating element; and a plurality of wick recesses formed in said heating block through which said wicks extend and are heated; and a control device connected to said heating elements for controlling the heat output of said heating elements.

15. The device of claim 14 wherein said control device includes a switch so that said heating elements can be deactivated or actuated together.

16. The device of claim 14 wherein said control device includes a switch so that said heating elements can be deactivated or actuated individually.

17. The device of claim 13 herein a first of said wick passages is associated with a first of heating elements to provide a first heating unit, and a second of said wick passages is associated with a second of heating elements to provide a second heating unit.

18. The device of claim 13 wherein said heating element includes an electric resistance element.

19. The device of claim 18 including a pair of electric resistance elements oppositely disposed on a heating block within said housing.

20. The device of claim 19 wherein said wick openings are located near the edge of said heating block and are centered between said heating elements.

21. The device of claim 18 wherein said electric resistance elements are rod-shaped.

22. The device of claim 14 wherein said heating block includes at least one thermal separator disposed between said wick openings for partial thermal disconnection of said heating units.

23. The device of claim 13 wherein said heating element has adjustable resistance values so that said heating element provides a plurality of heating capacities to adjust the evaporation rate.

24. The device of claim 23 including a control device for varying the output of said heating elements to control evaporation.

25. The device of claim 23 wherein said resistance elements are rod-shaped, and said resistance layer is spiral cut around said resistance body in a substantially helical manner.

26. The device of claim 25 wherein said resistance element is disposed within said heating block and encapsulated therein with a highly heat-conductive material.

27. The device of claim 26 wherein said resistance element is encapsulated within said heating block via a flame-resistant insulation having slits on either side of said resistance element through which electrical lines pass connecting said heating block to a connection plug.

28. The device of claim 13, wherein said housing comprises an upper shell and a lower shell, means for connecting said shells in a mating relationship, and said upper shell comprises a plurality of aeration slits for escape of the evaporated substances.

29. A device for the evaporation of volatile substances such as insecticides and aromatics comprising:

a housing;

a plurality of containers disposed in said housing for containing a volatile substance to be evaporated;

a plurality of wicks carried in said containers having wick ends protruding from said containers along a wick axis;

a heating unit carried in said housing for heating said wick elements; and said heating unit including a plurality of wick passages carried in said housing through which said wicks extend, and at least one heating element located in proximity to said wicks;

whereby a plurality of volatile substances may be evaporated from a housing in a controlled manner either to provide evaporation of different volatile substances or increased evaporation of a single substance.

* * * * *